United States Patent [19]

Giaever

[11] 4,011,308

[45] Mar. 8, 1977

[54] METHOD FOR SURFACE IMMUNOLOGICAL DETECTION OF BIOLOGICAL PARTICLES BY THE USE OF TAGGED ANTIBODIES

[75] Inventor: Ivar Giaever, Schenectady, N.Y.

[73] Assignee: General Electric Company, Schenectady, N.Y.

[22] Filed: Mar. 24, 1976

[21] Appl. No.: 670,043

Related U.S. Application Data

[63] Continuation-in-part of Ser. No. 430,884, Jan. 4, 1974, abandoned.

[52] U.S. Cl. .............................. 424/1.5; 23/230 B; 23/253 TP; 195/103.5 R; 250/320; 424/1; 23/230.3

[51] Int. Cl.[2] .................. G01N 23/00; G01N 33/16

[58] Field of Search .................... 424/1, 1.5, 12; 23/230 B, 253 TP; 195/103.5 R

[56] References Cited

UNITED STATES PATENTS

| | | | |
|---|---|---|---|
| 3,206,602 | 9/1965 | Eberle | 23/230 B |
| 3,592,888 | 7/1971 | Wolf | 424/1 |
| 3,646,346 | 2/1972 | Catt | 424/1 |
| 3,790,663 | 2/1974 | Garrison | 424/1 |
| 3,793,445 | 2/1974 | Updike | 424/1 |
| 3,826,619 | 7/1974 | Bratu | 424/1 |
| 3,843,775 | 10/1974 | Wolf | 424/1 |
| 3,935,074 | 1/1976 | Rubenstein | 23/230 B X |

OTHER PUBLICATIONS

L. E. M. Miles et al., The Lancet, No. 7566, 492–493, Aug. 31, 1968.
Chemical Abstracts, 68: 833c (1968).
"Hepatitis Associated Antibody (Anti–Australia Antigen)[125]/(Guinea Pig), Austria[tm]–125" a Abbott Laboratories pamphlet.

Primary Examiner—Morris O. Wolk
Assistant Examiner—Sidney Marantz
Attorney, Agent, or Firm—Leo I. MaLossi; Joseph T. Cohen; Jerome C. Squillaro

[57] ABSTRACT

The detection of immunologically reactive biological particles such as viruses, bacteria and other cells is obtained by detection of the occurrence of an immunological reaction on a substrate between the particle to be detected and its tagged antibody. A first immmunologically reactive biological particle is adsorbed onto the surface of the substrate in a particular monomolecular layer pattern, and the substrate is then exposed to a solution suspected of containing select particles to be detected which are specific to the first particle. Finally, the substrate is exposed to a medium containing tagged antibodies to the particle to be detected, and the pattern substrate surface is monitored for the presence of the tags by searching with a tag-sensing instrument for the particular pattern.

29 Claims, 3 Drawing Figures

(a)

(b)

U.S. Patent    Mar. 8, 1977    4,011,308
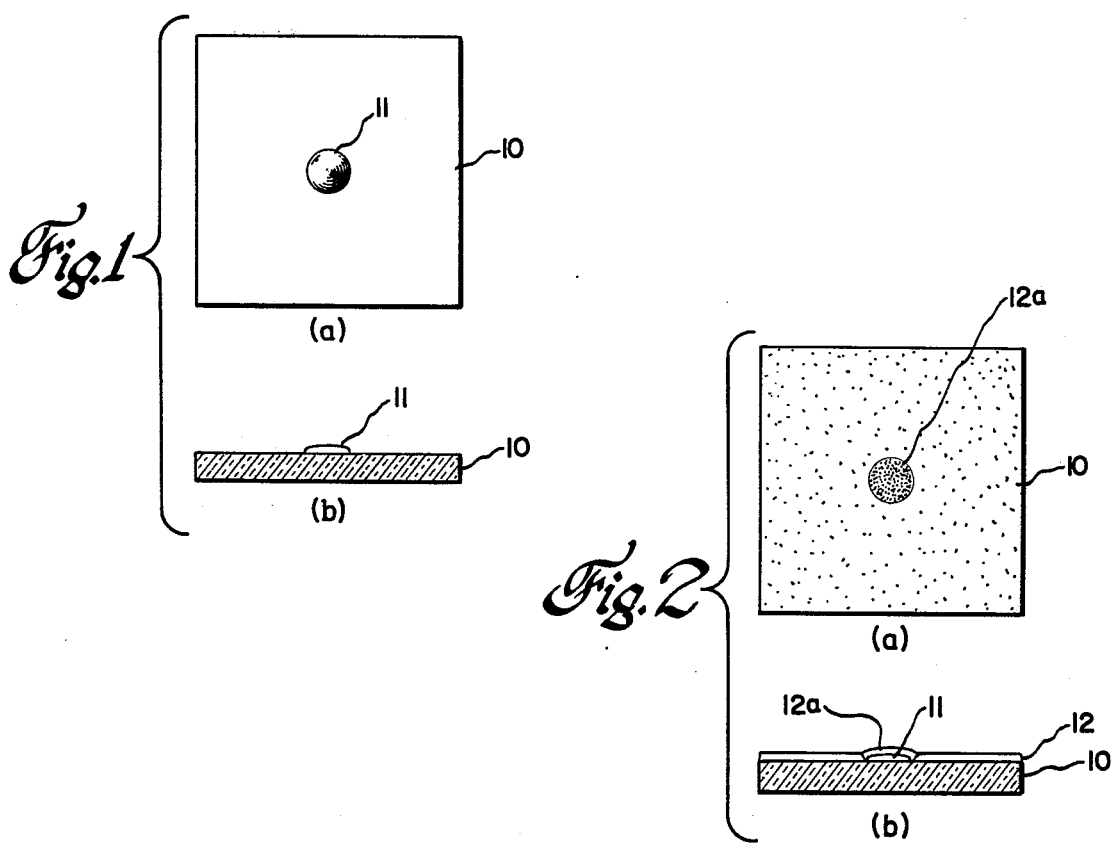
Fig. 1
Fig. 2
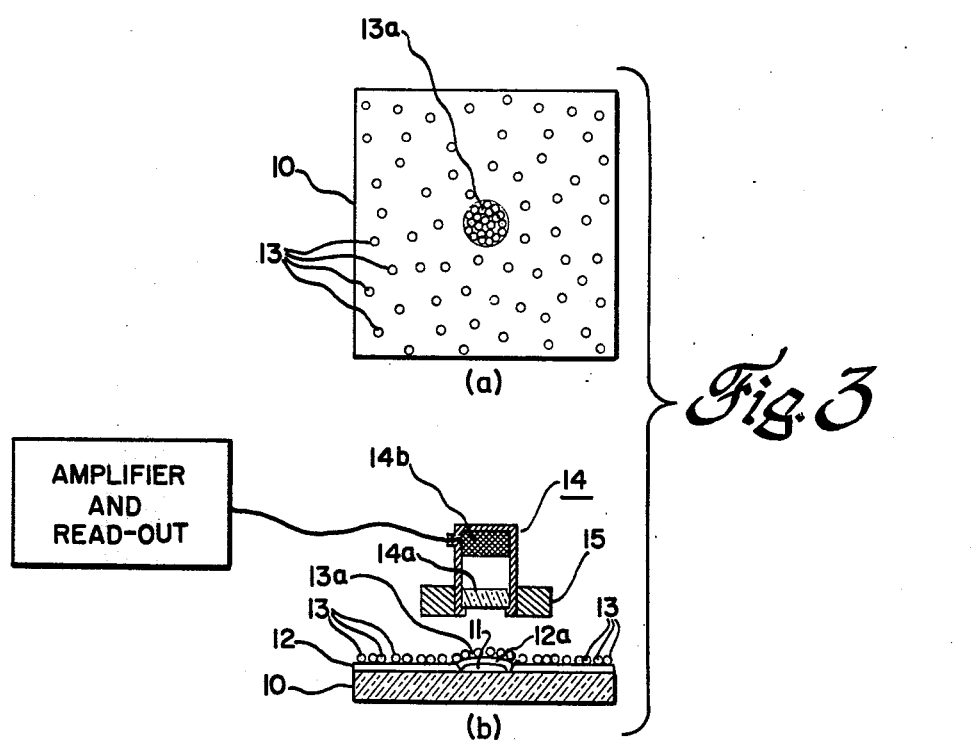
Fig. 3

METHOD FOR SURFACE IMMUNOLOGICAL DETECTION OF BIOLOGICAL PARTICLES BY THE USE OF TAGGED ANTIBODIES

This is a continuation-in-part of U.S. Pat. application Ser. No. 430,884 - Giaever, filed Jan. 4, 1974, now abandoned.

My invention relates primarily to a method and apparatus for detecting the occurrence of an immunological reaction between a biological particle and its tagged antibody, and in particular, to the method and apparatus for detecting the immunological reaction in a particular pattern on a suitable substrate.

This application is related to my copending applications Ser. No. 266,278, entitled, "Method and Apparatus for Detection and Purification of Proteins and Antibodies", filed June 26, 1972, now abandoned, Ser. No. 384,113 entitled "Improved Method and Apparatus for Detection and Purification of Proteins and Antibodies", filed July 30, 1973, now abandoned, and Ser. No. 573,610 entitled "Method for Detection of Biological Particles", filed May 1, 1975, and Ser. No. 388,407 entitled "Contrast Enhancement for Immunological Film Detection", inventor Golibersuch, filed Aug. 15, 1973, now U.S. Pat. No. 3,904,367, each application assigned as herein.

Other publications related to the present invention primarily as background are "The Antibody-Antigen Reaction: A Visual Observation", Ivar Giaever, *The Journal of Immunology*, Vol. 110, No. 4 (May 1973), pages 1424–1426 and "Three Simple Ways to Detect Antibody-Antigen Complex on Flat Surfaces", A. L. Adams et al., *Journal of Immunological Methods*, Vol. 3, (1973), pages 227–232 and U.S. Pat. No. 3,853,987, entitled "Immunological Reagent and Radioimmunoassay", issued Dec. 10, 1974 to William J. Dreyer, upon application Ser. No. 177,017, filed Sept. 1, 1971.

The term "biological particle" is intended to encompass smaller proteins (e.g., plasma proteins, antigens, antibodies, lactins) and bodies of proteinaceous material (e.g. viruses, bacteria, cells) capable of stimulating antibody production, when injected into an animal, and/or having the property of interacting specifically either immunologically or non-immunologically.

The term "tag" as used herein refers to an identifying molecule or group of atoms from which emanations occur, a. which can be chemically integrated into an entity that is itself difficult or presently impossible to detect in dilute concentrations and b. which, because of emanations therefrom, can be detected even in very small quantities by the use of appropriate instrumentation. Recognition of the tag (e.g. radioactive isotope, fluorescent group) automatically identifies the presence of the entity into which it is integrated.

Immunological reactions are highly specific biochemical reactions in which a first protein known as the antigen combines (links) with a second protein specific to the antigen and known as the antibody to form an immunologically complexed protein. Immunological reactions taking place within a biological system, such as an animal or human being, are vital in combatting disease. In a biological system, the entry of a foreign protein, i.e., the antigen, causes the biological system to produce the specific antibody proteins to the antigen in a process not fully understood at this time. The antibody protein molecules have available chemical combining or binding sites which complement those of the antigen molecule so that the antigen and antibody chemically link or bond to form an immunologically complexed protein.

Most antigens are proteins or contain proteins as an essential part, whereas all antibodies are proteins. Proteins are large molecules of high molecular weight, i.e., are polymers consisting of chains of variable numbers of amino acids. A given proteinaceous material will comprise entities (e.g., protein molecules, cells, etc.), which do not adhere to each other. Therefore, when a proteinaceous material is brought into contact with a substrate, it deposits as a single layer. If the entities are molecular in size, the resulting single layer is monomolecular; if the entities are larger, the layer will be a thicker single layer. No other arbitrary protein will adhere to a deposited protein layer. On the other hand, the specifically reacting protein to a protein adsorbed onto the substrate will immunologically bond thereto. In accordance with the teachings of the above-cited applications, this discovery is exploited to provide medical diagnostic apparatus in which a slide having a first layer of one protein adsorbed thereon is used to test suspected solutions for the presence of the specifically reacting protein thereto. If the specifically reacting protein is present in the solution, the slide after exposure to the solution has a double protein layer thereon. If the specifically reacting protein be absent from the solution, the slide after exposure to the solution has only the original layer thereon. Optical, electrical, chemical and tagged-detection means for distinguishing between the presence of double and single protein layers are taught in the related copending application and have different degrees of sensitivity and economy.

Because antibodies are produced by biological systems in response to invasions thereof by foreign proteins, the detection of antibodies in a biological system is of medical diagnostic value in determining the antigens to which the system has been exposed. A typical example of diagnostic detection of antibodies is the detection of antibodies to syphilis or gonorrhea in blood serum. Conversely, the detection of certain antigens in a biological system also has medical diagnostic value; examples of diagnostic detection of antigens include detection of HCG protein molecules in urine as a test for pregnancy, and detection of hepatitis-associated-antigen (HAA) molecules in the blood of prospective blood donors.

In order to perform such diagnostic tests, the appropriate protein of the immunologically reacting pair must be obtained. The only known source of an antibody protein is a living biological system. More particularly, only vertebrates are known at this time to exhibit immunological reactions to the introduction of a foreign protein. For example, many antibodies are found in the blood serum of animals and human beings which have been exposed to the corresponding antigens. Many antigens, however, may be controllably produced in laboratory cultures. However, some antigens, for example, hepatitis-associated-antigens, are at present, like antibodies, only obtainable from the higher living biological systems.

It is known in the immunological art that antibody molecules function as antigens when introduced into the system of a vertebrate to whom they are foreign proteins. Accordingly, specifically reacting antibodies to a given antibody may be readily produced in such vertebrate system.

While the emphasis herein for the purposes of simplicity and exemplification will be on immunologically reactive biological particles (the simplest case being the antigen-antibody pair), it should be understood as explained at the outset that my invention is equally useful with sets of biological particles that undergo forms of biological interaction other than an immunologic reaction, for example, the binding of enzymes to their biological substrates, or hemoglobin to haptoglobin, the only criterion being that the particles must be mutually specific.

Finally, it is also known in the immunological art (i.e. U.S. Pat. No. 3,826,619 - Bratu, Jr. et al) that a first biological particle such as an antigen (or antibody) can be attached to a solid surface, then be exposed to a solution suspected of containing a second biological particle to which the first particle is specific, and the system finally being exposed to a radioactive-tagged antibody to the second particle. The above technique appears to be that presently being utilized commercially and described in a pamphlet issued by Abbott Laboratories "Hepatitis Associated Antibody (Anti-Australia Antigen)$^{125}$/(Guinea Pig) AUSRIA - 125" to detect hepatitis by first coating the inner bottom surface of a first test tube with antibodies to HAA, then adding a blood sample suspected of containing HAA, and finally adding a radioactively-tagged antibody to HAA. A radiation counter is then used to test the total bottom surface of the first test tube for radioactivity obtaining an inseparable mixture of readout information plus background information. Since it is known that some nonspecific sticking of biological particles generally occurs in these tests, the magnitude of the non-specific sticking (background count) is obtained by repeating the test in both positive and negative control test tubes. The difference between the radiation counts of the first test tube and average of the control test tubes is then proportional to the concentration of the HAA in the suspect blood sample. However, the background count is generally about 25% of a "virus-present" count and thus the test results can often lead to confusion and reduced sensitivity. A further contribution to reduced sensitivity of the presently used test is due to the generally different characteristics of the test tubes resulting from the washing thereof. The washing process conducted especially after the blood sample has been added, in general, is not identical for the various test tubes and different degrees of specific sticking thereby remain in the tubes which vary the background counts. Thus, the presently used radioimmunoassay test is not consistently satisfactory and suffers from unnecessarily low sensitivity.

Fluorescent tagging in an alternative to radioactive tagging and other forms of tagging will occur to those skilled in the art. Thus, for example, it is known in the immunological arts to prepare antibodies to human immunoglobulins for chemical combination with fluorescent organic molecules such as the isothiocyanates. This tagged antibody is then used to render an immunological reaction visible by ultraviolet microscopy, particularly in the serological test for syphilis after the method of Coons, now known in the art as FTA-STS procedure. In the FTA-STS procedure, a quantity of *Treponema pallidum* (*T. pallidum*) is dried on a slide. The slide is then immersed in a blood specimen. The slide is subsequently immersed in a solution of tagged immunoglobulin. The anti-human immunoglobulin does not bond to the *T. pallidum;* accordingly, the slide will fluoresce, when observed by ultraviolet microscopy only if the specimen contained antibodies to T. pallidum.

The presently preferred tags are radioactive ones, for instance, iodine 125 (designated I-125 or $^{125}$I).

Briefly, in order to achieve the objects of my invention, I provide a method and apparatus for the detection of immunologically reactive biological particles such as viruses, antigens, antibodies, bacteria and other cells by detection on a substrate of the occurrence of an immunological reaction between the particle to be detected and its tagged (i.e., radioactive-tagged) antibody. A first immunologically reactive biological particle is adsorbed onto the surface of the substrate in a particular mono-molecular layer pattern. The first particle pattern-coated substrate is then exposed to a solution suspected of containing the select particles (i.e., the particles to be detected), which are specific to the first particles. Finally, the coated substrate is exposed to a medium containing tagged antibodies to the second particle and the substrate surface is monitored for tag emanation by searching for the relatively high level of emanation from the triple layer which is present in the pattern area, if the solution does contain the second particles, in a direct test embodiment of my invention. Alternatively, in an indirect test embodiment of my invention, the first biological particle pattern applied to the substrate is a purified form of the select particle to be detected, and antibodies to the first particle are mixed in the solution to be tested for the select particle, which is of the same nature as the first particle, prior to exposing the substrate to this solution. The final step consists of exposing the coated substrate to a radioactive-tagged third particle which is, in general, an antibody to the antibodies added to the test solution. The results of the tests for radioactivity are opposite for the direct and inhibition tests; in the direct test a radiation count in excess of the background count indicating presence of the particle suspected to be in the solution being tested, and merely a background count indicating absence of such particle, whereas in the inhibition test the greater radiation count indicates absence of the particle. The adsorbing of the first biological particles in a particular pattern on the substrate obtains subtantially improved sensitivity over the conventional procedure wherein the whole surface of a test tube is radiation monitored and therefore subject to considerable background which confuses the results. My detection method and apparatus is much more economical over the conventional radioimmunossay test in both time and cost since only a single slide is required per test.

The features of my invention which I desire to protect herein are pointed out with particularity in the appended claims. The invention itself, however, both as to its organization and method of operation together with further objects and advantages thereof, may best be understood by reference to the following description taken in connection with the accompanying drawing wherein like parts in each of the several figures are identified by the same reference character, and wherein:

FIG. 1 schematically presents plan and elevational views of a substrate after a first biological particle is adsorbed on its surface in a particular first layer pattern;

FIG. 2 schematically presents plan elevational views of the substrate after it has been exposed to a solution suspected of and, in fact, containing the second biological particle; and FIG. 3 schematically presents plan and elevational views of the substrate after it has been exposed to the tagged antibody to the second particle and the pattern is being tested for the presence of tags.

The best mode contemplated for the invention is the use of radioimmunoassay and, therefore, the following description employs, but the invention is not restricted to, radioactive tagging.

Referring now to FIG. 1, there is shown in the plan view a and the elevation view b thereof, a substrate 10 having a substantially flat top surface and being fabricated of a suitable material which may be metal, glass, plastic or similar material, and preferably is in the form of a metal or metallized glass slide. After selection of a substrate suitable for the particular immunological test to be conducted, the next step in my method for surface immunological detection of immunologically reactive biological particles by radioimmunoassay consists of depositing a first single layer of immunologically reactive biological particles on the top surface of substrate 10 in a particular pattern. The first biological particle is selected in accordance with its capability of being specific to the particular (select) biological particle being investigated. The first particle may be produced in laboratory cultures or obtained from the higher living biological systems, as determined by the nature of the particular first particle. A convenient pattern for the single layer of the first biological particles on substrate 10 is the generally circular shape obtained by depositing a single drop of a first solution of the first biological particles on the surface of substrate 10. The solution may be a salt solution of water or other liquid appropriate to, and nonreactive with, the particular first biological particles which preferably are in highly purified form. The drop of the first solution is maintained on the substrate surface for a time interval sufficient so that the first biological particles become adsorbed onto the surface of substrate 10 in a substantially complete single layer in the particular circular pattern of the drop (e.g., in accordance with the teachings in the aforementioned co-pending U.S. patent application of Giaever). The time interval for the formation of the single layer on substrate 10 is an inverse function of the concentration of the first particles in the solution. A typical circular pattern of the single layer 11 is shown in view a of FIG. 1 and in highly magnified view in view b of FIG. 1. The remaining top surface of substrate 10 remains clean after the circular-shaped single layer pattern 11 has formed thereon. The area size of the layer pattern 11 is preferably as small as practicable, and is generally in the range of one square millimeter to one square centimeter in order to conserve the amount of biological material used in the three single superimposed layers in accordance with the method to be described hereinafter. A consideration in utilizing a small pattern for layer 11 is that the process for producing the first (and third) biological particles may be time-consuming and, or expensive and therefore it is highly desirable to economize on their use. Depending upon the solution of the first biological particles, a washing of the surface of substrate 10, especially in the region of first layer 11 may be utilized after the formation of the particular pattern layer on the substrate surface.

After the single layer pattern 11 has formed on substrate 10, the substrate surface is dried, preferably by blowing air at room temperature across the substrate in order to speed the drying process. The pattern layer-coated substrate 10 is next exposed to a second solution suspected of containing the select immunologically reactive biological particles, which are the subject of the particular test being conducted. The exposure is generally accomplished by immersing the coated substrate in the second solution and the immersion time interval is again an inverse function of the concentration of the second biological particles in the second solution. Since the concentration of the select particles is generally much less than the concentration of the first particles in the first solution, the immersion step in the second solution is generally much longer than the time interval for forming the first single layer 11. The first biological particles are specific to the select particles so that the presence of the latter in the second solution forms another substantially complete single layer 12a along the pattern established on substrate 10 by the first layer 11 as a result of the immunological reaction wherein the select particles become bound to the first particles. If all of the top surface of the substrate 10 is exposed to the second solution, the second single layer is formed on such top surface and over the pattern region, such layer along the non-patterned region being designated by numeral 12 in view b of FIG. 2. The single layer 12 in direct contact with the surface of substrate 10 results from random, non-specific sticking to the substrate surface of other (i.e., non-specific) protein entities present in the second solution, whereas the portion of the second layer which forms along the pattern of the first monomolecular layer 11 (designated 12a) forms a double layer with layer 11, as illustrated in view b of FIG. 2. The random, non-specific sticking, more clearly shown by the random dots in view a of FIG. 2 is a nondesired, but unavoidable occurrence which, after a subsequent step of exposing the substrate to radioactive-tagged biological particles, causes an undesired background radiation count. However, as depicted in this view, it should be noted that the protein molecules which attach to the surface of substrate 10 as a result of the nonspecific sticking are of much smaller number and widely spaced as compared to the substantially complete layer 12a of the select particles.

After the substrate 10 has been sufficiently exposed to the select biological particles, the substrate is removed from the second solution suspected of containing such particles and is washed by a suitable solution which, in many cases, may be water or a salt solution thereof, for purposes of removing much of the non-specific particles which had stuck to the substrate. The substrate is subsequently exposed to a medium containing a quantity of a third biological particle which is radioactive-tagged and is, in general, an antibody to the select biological particle. In any event, the radioactive-tagged third biological particle is specific to the select biological particle so that presence of the latter on substrate 10 causes the third particles to complex therewith and form a third single layer 13a on substrate 10 in the particular pattern of the first layer 11, as illustrated in FIG. 3, and especially in view b of FIG. 3. The exposure of substrate 10 to the third biological particles can be accomplished by immersion in a third solution of such particles or by being coated with the third solution in the case of a sufficiently high concentration thereof. Again, the length of the exposure of the substrate to the third solution, in order to obtain a substantially complete pattern layer 13a, is primarily a function of the concentration of such particles in the third solution. The concentration of the third particles can again be controlled, as in the case of the first particles, since these particles are produced in laboratory cultures or in the higher living biological systems. Thus the concentration employed is generally much higher than the concentration of the select particles in the second solution. In such a case the time interval of exposure to the third particles is much less than the immersion step in the second solution. Some of the nonspecific particles which remain stuck on substrate 10 in the field around the pattern area from the second solution also complex with the radioactive-tagged third particles, as schematically indicated by the widely and random-spaced small circles 13 shown in views a and b of FIG. 3, and such radioactive-tagged third particles form the background radiation count in the subsequent radiation count measurement. After the desired three-layer pattern layer consisting of single layers 11, 12a, and 13a bound together has been established on substrate 10 (assuming the second solution contained the select immunologically reactive particles), the substrate is removed from the source of the radioactive-tagged third biological particles and a suitable radiation counter 14 is then positioned in close proximity to the coated surface of substrate 10 which is then monitored for radioactivity. The monitoring step involves searching the surface of substrate 10 for the relatively high radiation level emitted from the three layer pattern on substrate 10, if the select particles are present in the second solution. In the searching process, the relatively low radiation level corresponding to the background count is measured, and the presence of the three layer pattern is readily apparent due to the sudden increase in the radiation level associated therewith. The counter aperture is adjusted so that the counter is responsive only to an area approximately the area of the initial pattern 11. The aperture adjustment may be made, for example, by utilizing a lead shield 15 at the input end of radiation counter 14 and the shield 15 is provided with an aperture conforming to the desired counter aperture. If the emanations from the radioactive-tagged third biological particles are primarily gamma rays, the radiation counter 14 may be a conventional gamma ray counter comprising a tubing having a scintillator crystal 14a at the aperture end thereof and a photocathode 14b at the output end. The voltage bias connections in counter 14 are not shown for purposes of simplicity. The scintillator crystal 14a may be fabricated of sodium iodide as one example, is responsive to the gamma rays impinging thereon, and emits light photons which are detected by the photocathode 14b and converted to voltage pulses corresponding to the number of counts detected. The output of photocathode 14b is connected to a suitable electronic amplifier (not shown) for amplifying the voltage count pulses, and the output of the amplifier is applied to the input of a suitable real time read-out device (not shown) which may provide a visual (oscilloscope) or audible (loudspeaker) output or may be a memory storage device such as magnetic tape for permitting a delayed read-out. If the emanation from the radioactive-tagging are beta rays, the radiation counter 14 may be a conventional beta ray counter comprising a sealed tubing which is gas filled and has an electrode therein connected to a source of relatively high voltage such that the beta rays ionize the gas and each gas ionization event is detected by the electronic amplifier and read-out device.

Alternatively, the emitted radiation can be detected by the autoradiography technique wherein a special photographic film sensitive to gamma rays is placed directly on top of the coated substrate 10. Presence of the three-layer deposit is readily apparent on such film as a much higher level of exposure as compared to the background exposure level.

As a specific example of the application of my invention, there will first be considered the direct test for hepatitis. In this test, the first biological particle is the antibody for HAA which is generally in a solution of salt water or inert serum. The drop of the first solution (and any additional drops thereof which may be necessary depending on the concentration of the antibody) is maintained on the surface of the diagnostic slide (substrate 10) for a period of approximately one hour for a concentration of 10 micrograms/cc solution, and ten minutes for a concentration of 100 micrograms/cc in order to develop a complete or nearly complete monomolecular pattern layer 11. The select biological particle is the hepatitis-associated-antigen (HAA) contained in a blood serum sample of a patient suspected of having hepatitis. This concentration may be in the order of 1 nanogram/cc serum, if the patient does in fact have hepatitis, and the slide remains immersed in such blood serum sample for approximately 24 hours to produce the second single layer. The third biological particle is a radioactive-tagged antibody to the HAA which may be the same antibody as the first biological particle, and has been produced by the same, or a different process. The radioactive-tagging element is typically the iodine isotope I-125.

Typically, the HAA antibody is developed in a goat, rabbit, or other suitable animal by injection thereof with the HAA, waiting a suitable incubation period such as two weeks, and then drawing blood, containing the specific antibody, from the animal and separating the antibody from the remaining blood proteins. The exposure time interval of the slide to the radioactive-tagged antibody for the deposit of a monomolecular layer is approximately one hour for a concentration of 10 micrograms/cc salt water or other inert serum, and 10 minutes for a concentration of 100 micrograms/cc. The diagnostic slide is then tested for radioactivity, and the detection of a small region having a radiation level substantially greater than the background radiation count existing along the remaining surface of the slide indicates that the patient does have hepatitis. Absence of the region of higher radiation count indicates absence of the HAA in the blood serum sample.

In an indirect test for hepatitis, the first biological particle is the hepatitis-associated-antigen which forms the particular single layer pattern 11 on substrate 10, the select biological particle is the antibody to HAA, and the third biological particle is a radioactive-tagged contibody to the antibody to HAA, the latter, in general, being produced in the animals as noted above after an interval of approximately two weeks after injection thereof with the pure antibodies from the human serum. In the indirect test, the sample of blood to be tested for hepatitis is mixed with the antibodies to the HAA so that any HAA in the blood sample complexes with the added antibodies in the second step and when such mixture is then applied to the pattern 11 on the substrate 10, the effect is opposite to that obtained in the direct test, i.e., in the case of the presence of HAA in the blood serum, no second single layer 12a is produced over pattern 11.

In the case of a direct test for syphilis or gonorrhea, the object is to look for antibodies to such diseases in the patient being examined. In the syphilis test, the first biological particle is the antigenic site from the syphilis spirochetes (such as the Reiter protein antigen) which functions as an antigen to form the particular layer pattern 11 on substrate 10, the select biological particle is the antibody to the syphilis disease which may be present in the blood serum specimen taken from the patient, and the third biological particle is the radioactive-tagged antibody to the antibody to the syphilitic disease which again may be produced in a suitable animal.

From the foregoing description, it can be appreciated that my invention makes available a new method and apparatus for the surface immunological detection of biological particles by tagging in which, when the substrate surface is tested for tag emanations, a particular pattern within a substrate field is searched for, rather than merely counting the sum of the tag emanations for the whole substrate, thereby obtaining a much more sensitive test due to the substantial contrast in emanation levels when the particular pattern is present as compared to the background emanations in the surrounding field. The immunological test can be performed with virtually any protein that is capable of immunological complexing with another protein and thus includes antigens, antibodies, viruses, bacteria, hormones, enzymes and other cells which can be readily grown or otherwise isolated and collected.

Since my test can be performed on a single substrate, my method is a substantial improvement as, for example, over the prior art radioimmunoassay referred to hereinabove in which a test tube is used for the specimen being tested and a plurality of positive and negative control test tubes are required for determining an average background radiation count, because this prior art technique involves counting the sum of the radioactivity for the whole test tube. My method is therefore much more economical in terms of the amount of apparatus required and the testing procedure is therefore much more simplified. But, the most important feature of my invention is the significant increase in sensitivity provided by the use of a preselected pattern for the first layer and the benefits of contrast, shape and specific location afforded thereby. This increased sensitivity avoids the often serious problem of having to make a determination as to whether a relatively low radiation count is due merely to background or to the presence of a low concentration of the particular biological particles for which the test is being conducted.

Also, in the aforementioned prior art immunoassay method the parts of the apparatus for the test and controls are subjected to a series of handling steps including washing and rinsing. If these steps are not carried out in exactly the same manner in the test and controls (i.e., the extent of washing; the extent of rinsing), error is inevitably introduced. This problem is avoided in the instant invention in which a single substrate is used.

The immunological detection method in accordance with my invention is especially important for hormone testing since hormones are generally present in very low levels. The immunological (indirect) testing for a hormone utilizes a pure form of the hormone as the first biological particle and, due to the small area of the preselected pattern required does not require a significant amount of the hormone. The blood sample to be tested for the hormone is mixed with antibodies to such hormone, these antibodies being obtained from human blood serum from a person known to have such hormone in his system. Finally, the radioactive-tagged antibodies to the antibodies to the hormone are obtained from an animal of the type mentioned above which has previously been injected with antibody to the hormone.

Having described my invention with reference to particular embodiments and examples, it is believed obvious that modification and variation of my invention is possible in the light of the above teachings. Thus, tags other than radioactive tags may be employed.

Also, a blood serum sample can be quantitatively determined using the indirect procedure for a particular biological particle in a simple variation of my invention in the following manner. A plurality of containers of equal size sufficient to receive one of the substrates, e.g. diagnostic slides in each container, are utilized, a plurality of four being a convenient number. Each slide is exposed in the same manner to the same concentration of a particular first biological particle in purified form, for example, a hormone, for which the quantitative test is to be established in order to obtain substantially the same size monomolecular layer pattern (of the first biological particle) thereon corresponding to layer 11. The blood serum sample to be assayed for the hormone is divided into four equal parts, and various known concentrations (i.e., $a$, $2a$, $4a$, $8a$) of a radioactive-tagged antibody to the given hormone are respectively added to the four blood samples for complexing with some or all of the hormone in the blood serum in the separate parts of the blood samples to the extent of the concentration of antibody added. The four mixtures are then respectively added to the four containers, and after a suitable interval the four slides are removed and tested for radioactivity. The hormone concentration is then quantitatively determined as being between the concentrations ($a$, $2a$, $4a$, $8a$) at which substantial radiation is first detected and the next lower concentration. Obviously, the mixtures could be made in the containers, and the monomolecular pattern coated slides then immersed in the containers. This test, therefore, only utilizes a double layer as distinguished from the triple layer in the previous tests enumerated above. Also, it should be understood that the previous tests also provide a quantitative measurement of the concentration of the suspect particle by the level of the radiation detected in the pattern. It is, therefore, to be understood that changes may be made in particular embodiments of my invention as described herein which are within the full intended scope of the invention as defined by the following claims.

What I claim as new and desire to secure by Letters Patent of the United States is:

1. A method for determining the presence or absence of select biological particles in a liquid sample comprising the steps of:

contacting a portion of the surface area of a substrate with first biological particles specific to the select biological particles, said first biological particles being dispersed as a first single layer coating said portion of said surface area in the form of a preselected pattern;

contacting at least the coated surface area of said substrate with the sample liquid for a preselected period of time;

applying a liquid medium to the coated surface area resulting from the preceding step;

said liquid medium containing tagged biological particles specific to the select biological particles, the tags for said tagged biological particles being detectable by determining the presence of emanations therefrom and monitoring the level of tag emanations over said surface area to determine whether said level is significantly greater over said preselected pattern than over the balance of said surface area.

2. The method set forth in claim 1 wherein the substrate consists of a metallized glass slide.

3. The method set forth in claim 1 wherein the substrate consists of a glass slide.

4. The method recited in claim 1 wherein the contacting with first biological particles to provide the preselected pattern is accomplished by the deposit on the substrate of a drop of solution containing said first biological particles, said preselected pattern being of generally circular area.

5. The method set forth in claim 4 and further comprising the step of drying the drop of solution deposited on the substrate.

6. The method recited in claim 1 wherein contact with the sample liquid is accomplished by immersing the coated substrate therein.

7. The method recited in claim 1 further comprising following the contacting with sample liquid by the step of washing the coated surface area of the substrate sufficiently to remove non-specific particles.

8. The method set forth in claim 1 wherein the liquid sample is a blood serum sample from a patient suspected of having the select biological particles in his blood stream.

9. The method recited in claim 1 wherein the coated substrate is immersed in a liquid medium of predetermined content of tagged biological particles.

10. The method set forth in claim 1 wherein the first biological particles are protein.

11. The method set forth in claim 1 wherein the first biological particles are antigen.

12. The method set forth in claim 1 wherein the first biological particles are antibody to the select biological particles.

13. The method set forth in claim 12 wherein the select biological particles are antigen.

14. The method set forth in claim 1 wherein the select biological particles are protein.

15. The method set forth in claim 1 wherein the select biological particles are antibody to the first biological particles.

16. The method set forth in claim 1 wherein the select biological particles are viral.

17. The method set forth in claim 1 wherein the select biological particles are bacterial.

18. The method set forth in claim 1 wherein the select biological particles are hormonal.

19. The method set forth in claim 1 wherein the select biological particles are enzyme in nature.

20. The method set forth in claim 1 wherein the tagged biological particles are protein.

21. The method set forth in claim 1 wherein the tagged biological particles are antibody to the select biological particles.

22. The method recited in claim 1 wherein the tagged biological particles are radioactive-tagged.

23. The method recited in claim 22 wherein the monitoring step is conducted with a radiation counter suitable for detecting the type of emanations from the tags.

24. The method recited in claim 22 wherein the monitoring step employs autoradiography.

25. The method recited in claim 1 wherein the area of the preselected pattern is in an area range of from about one square millimeter to about one square centimeter.

26. The method recited in claim 1 wherein the tagged biological particles are biological particles with which fluorescent molecules have been chemically integrated.

27. The method recited in claim 26 wherein the fluorescent molecules are organic in nature.

28. An indirect test for determining the presence or absence of select biological particles in a liquid sample comprising the steps of:

contacting a portion of the surface area of a substrate with the select biological particles, said select biological particles being dispersed as a first layer coating said portion of said surface area and defining a preselected pattern;

contacting at least the coated surface area of said substrate with the sample liquid for a preselected period of time, said liquid sample having previously had added thereto first antibodies specific to said select biological particles;

applying a liquid medium to the coated surface area from the preceding step, said liquid medium containing tagged antibodies specific to said first antibodies, the tags for said tagged antibodies being detectable by determining the presence of emanations therefrom and monitoring the level of tag emanations over said surface area to determine whether said level is significantly greater over said preselected pattern than over the balance of said surface area.

29. A method for quantitative testing for the presence of a select immunologically reactive biological particle comprising the steps of introducing into each of a plurality of containers a mixture of a portion of a blood sample to be tested for the select biological particle together with tagged antibodies thereto, each container receiving a different known concentration of said tagged antibodies, exposing a like plurality of substrates to select biological particles, said select biological particles being dispersed as a first layer on each substrate defining a particular pattern covering a portion of said substrate, contacting the layer on each substrate with mixture from a separate one of said containers, maintaining the contact for an interval sufficient to allow radioactive-tagged antibodies which remain noncomplexed in the portions of blood sample to become complexed with the layer of select biological particles on each substrate to form a second layer thereover in said particular pattern, monitoring the level of tag emanations over the surface of each substrate to ascertain whether said level is significantly greater over the particular patterns than over the adjacent substrate area, and determining the concentration of the select biological particle by noting in the order of change of concentration of the tagged antibodies the two slides at which a change is encountered from insignificant presence of tags to substantial presence of tags.

* * * * *